United States Patent
Hovanes et al.

(10) Patent No.: US 7,485,131 B2
(45) Date of Patent: *Feb. 3, 2009

(54) SYSTEM AND METHOD FOR CONTROLLING PRESSURE IN A SURGICAL TOURNIQUET

(75) Inventors: Michael E. Hovanes, Redmond, WA (US); Don S. Schmitt, Wauwatosa, WI (US)

(73) Assignee: Stryker Corporation, Kalamzoo, MI (US)

( * ) Notice: Subject to any disclaimer, the term of this patent is extended or adjusted under 35 U.S.C. 154(b) by 458 days.

This patent is subject to a terminal disclaimer.

(21) Appl. No.: 10/631,019

(22) Filed: Jul. 30, 2003

(65) Prior Publication Data

US 2004/0147956 A1    Jul. 29, 2004

Related U.S. Application Data

(63) Continuation-in-part of application No. 09/955,763, filed on Sep. 19, 2001, now Pat. No. 6,605,103, which is a continuation-in-part of application No. 09/504,131, filed on Feb. 15, 2000, now Pat. No. 6,475,228, which is a continuation-in-part of application No. 09/280,312, filed on Mar. 29, 1999, now Pat. No. 6,051,016.

(51) Int. Cl.
   *A61B 17/12* (2006.01)
(52) U.S. Cl. .................................... 606/202
(58) Field of Classification Search ........... 606/201, 606/202, 203, 204; 601/150, 148, 149
   See application file for complete search history.

(56) References Cited

U.S. PATENT DOCUMENTS

| 4,321,929 | A | 3/1982 | Lemelson et al. |
| 4,469,099 | A | 9/1984 | McEwen |
| 4,479,494 | A | 10/1984 | McEwen |
| 4,605,010 | A | 8/1986 | McEwen |
| 4,671,290 | A | 6/1987 | Miller et al. |
| 4,770,175 | A | 9/1988 | McEwen |
| 4,869,265 | A | 9/1989 | McEwen |
| 5,048,536 | A | 9/1991 | McEwen |
| 5,181,522 | A | 1/1993 | McEwen |
| 5,307,791 | A | 5/1994 | Senoue et al. |
| 5,312,431 | A | 5/1994 | McEwen |
| 5,352,195 | A | 10/1994 | McEwen |
| 5,366,474 | A | 11/1994 | Blumenkanz et al. |
| 5,439,477 | A | 8/1995 | McEwen |
| 5,454,831 | A | 10/1995 | McEwen |
| 5,556,415 | A | 9/1996 | McEwen et al. |

(Continued)

*Primary Examiner*—Kevin T Truong
(74) *Attorney, Agent, or Firm*—Howard & Howard Attorneys, P.C.

(57) ABSTRACT

A system and method of controlling the pressure within a pressure cuff of a surgical tourniquet so as selectively to occlude blood flow within a portion of a limb of a patient, wherein a sensor determines when flow past the tourniquet is occurring so that corrective action may be taken, such as by increasing the pressure in the tourniquet or by notifying an operator of the flow past the tourniquet. The present invention may use an acoustic sensor to detect Korotkoff sounds indicating incipient blood flow past the tourniquet. When such signals are detected, the tourniquet controller may either incrementally increase the pressure in the tourniquet, or if a threshold would be exceeded by such an increase, signal an alarm indicative of the blood flow.

19 Claims, 11 Drawing Sheets

U.S. PATENT DOCUMENTS

| | | | |
|---|---|---|---|
| 5,578,055 A | 11/1996 | McEwen | |
| 5,584,853 A | 12/1996 | McEwen | |
| 5,607,447 A | 3/1997 | McEwen et al. | |
| 5,649,954 A | 7/1997 | McEwen | |
| 5,681,339 A | 10/1997 | McEwen et al. | |
| 5,741,295 A | 4/1998 | McEwen | |
| 5,855,589 A | 1/1999 | McEwen et al. | |
| 5,911,735 A | 6/1999 | McEwen et al. | |
| 5,968,073 A * | 10/1999 | Jacobs | 606/202 |
| 6,589,267 B1 * | 7/2003 | Hui | 606/202 |
| 6,605,103 B2 * | 8/2003 | Hovanes et al. | 606/202 |
| 7,166,123 B2 * | 1/2007 | Hovanes et al. | 606/202 |

\* cited by examiner

SYSTEM AND METHOD FOR CONTROLLING PRESSURE IN A SURGICAL TOURNIQUET

The present application is a continuation in part of U.S. patent application Ser. No. 09/955,763, filed Sep. 19, 2001 issued as U.S. Pat. No. 6,605,103 on Aug. 12, 2003, which is a continuation in part of U.S. patent application Ser. No. 09/504,131, filed Feb. 15, 2000 now U.S. Pat. No. 6,475,228 which is a continuation of U.S. patent application Ser. No. 09/280,312. U.S. patent application Ser. No. 09/280,312 filed Mar. 29, 1999 issued as U.S. Pat. No. 6,051,016 on Apr. 18, 2000.

FIELD OF THE INVENTION

The present invention relates generally to surgical tourniquets. More particularly, the present invention relates to various aspects of a system and method for controlling pressure in a surgical tourniquet utilizing feedback from a flow detection sensor incorporated in the tourniquet control system.

BACKGROUND

Surgical tourniquets are widely used during surgical procedures to occlude the flow of blood in a portion of a limb during the procedure, particularly in connection with arthroscopic procedures relating to the hand, wrist, elbow, foot, and knee, in which the existence of a bloodless field in the appropriate portion of a patient's limb may be required. Surgical tourniquets are similarly useful in other procedures in which the creation of a bloodless field is desirable, including nerve grafting and harvesting. It is important that pressure be maintained by a surgical tourniquet despite the manipulation by a surgeon of the limb on the elevation of blood pressure due to an autonomic nervous response in which blood flow is being occluded, where the manipulation tends to affect the pressure within the tourniquet and the pressure distribution of the tourniquet on the extremity. Also, it is important that the tourniquet pressure be minimized to reduce the potential of adverse effects due to the constriction of the tourniquet. It is also important that the surgical tourniquet be easy to use and physically stable so that the surgeon may focus his attention on other aspects of the surgery.

Typical non-invasive blood pressure measurements are generally made by either of two methods. In the first method, a stethoscope is placed beneath or below a pressure cuff. The pressure cuff is then inflated to a pressure in excess of the patient's systolic blood pressure, causing occlusion of the blood flow past the pressure cuff. The pressure in the cuff is then gradually decreased, while a person taking the pressure measurement listens through the stethoscope. As the blood pressure overcomes the pressure in the cuff, blood begins flowing past the cuff. This blood flow causes sounds called Korotkoff sounds to be generated. These sounds are distinctive of the blood flow past the pressure cuff, and abate once the blood pressure fully reopens the arteries constricted by the pressure cuff. By identifying the Korotkoff sounds, and monitoring the decreasing pressure in the cuff, the pressure at which blood pressure exceeds cuff pressure can be identified. Determinations can be made of both systolic and diastolic blood pressures by monitoring Korotkoff sounds associated with a higher pressure (systolic) and a lower pressure (diastolic). This method is sometimes referred to as the auscultatory method.

A second method of non-invasive blood pressure measurement, called oscillometric measurement, is also accomplished using a pressure cuff and decreasing pressure. In oscillometric pressure measurement, however, a column of mercury is generally used to measure the pressure in the cuff. As the patient's blood pressure exceeds the cuff pressure, blood flow past the cuff causes the pressure in the cuff to pulse in time with the blood flow past the cuff. The mercury column being used to measure pressure thus also pulses, allowing a person taking the blood pressure measurement to visually identify blood flow past the pressure cuff. The patient's blood pressure can thus be determined by monitoring the mercury column for the start of pulsing, and the pressure at which the pulsing begins.

Recently, measurement of oxygen levels in blood (such as used in pulse oximetry) has been shown to be a reliable indicator of blood flow past a tourniquet. As the effectiveness of the tourniquet decreases, the oxygen level of blood downstream of the tourniquet increases. This effect may occur before the flow is sufficient to create flow noises, such as those utilized for ausclutic or oscillometric determination of blood flow past a tourniquet. This effect is sometimes referred to as "pinking up" of the blood.

Blood oxygen levels may be determined non-invasively through photometric methods which use reflected and/or refracted light to evaluate oxygenation of the blood. Monitors for determining oxygenation may be placed against the skin of a patient to whom a tourniquet has been applied, allowing measurement of the oxygen saturation level of the blood at that site to be measured.

The pressure necessary to occlude blood flow in a tourniquet is dependant on the blood pressure of the patient on whom the tourniquet is applied. When the pressure of the tourniquet exceeds the blood pressure, the heart of the patient is unable to pump blood past the tourniquet location. Typically, the tourniquet pressure cuff is inflated in excess of the blood pressure to ensure occlusion of blood flow past the tourniquet. When a surgical tourniquet is applied to the arm, over-pressurization of the surgical tourniquet of 50-75 mm Hg is common. When a surgical tourniquet is applied to a leg, over-pressurization of the surgical tourniquet of 75-100 mm Hg is common.

Over-pressurization of a tourniquet can cause injury to a patient on whom the tourniquet is being used. Neural and vascular injuries can occur due to the pressure in use causing physical trauma. Accordingly, the pressure used to occlude blood flow past the tourniquet should be kept to the minimum necessary to overcome the systolic pressure, thus preventing the pumping of blood past the tourniquet. Contrarily, high pressures ensure occlusion of blood flow.

In addition to the constraints of simply using a surgical tourniquet to occlude blood flow, the use of the surgical tourniquet to provide a barrier to allow intravenous regional anesthesia (IVRA) raises additional concerns, particularly with the dangers associated with the flow of the anesthesia past the barrier and into the body of the patient. Furthermore, the need to flush metabolized anesthesia from the limb at the conclusion of an operation requires the allowance of systolic flow to both test veins and arteries potentially affected by the surgery, and to displace remaining anesthesia and its metabolized by-products.

SUMMARY OF THE INVENTION

The present invention is directed towards a system and method for controlling the pressure within a surgical tourniquet so as to occlude blood flow past a tourniquet. The surgical tourniquet uses a fluid medium to vary the pressure within the tourniquet. The fluid medium may be air. The addition or removal of air from the surgical tourniquet is controlled such as through a controller described in our patent applications, Ser. Nos. 09/280,312 and 09/504,131, herein incorporated in their entirety by reference thereto.

The flow of blood past a tourniquet may create an indication which may be detected and transmitted to a tourniquet controller. The indication may be pressure variations in the veins and arteries of an extremity to which the surgical tourniquet is applied. These pressure variations may be a signal audible to a listener, or a variation of the cuff pressure caused by the pulsing associated with normal blood flow. These pressure variations may be transmitted from the surgical tourniquet to the controller via the fluid medium used to inflate the tourniquet. By incorporating a sensor to detect these signals, a feedback loop can be incorporated into the controller allowing the controller to detect blood flow past the tourniquet when the tourniquet is inflated. When blood flow past the pressure cuff of the surgical tourniquet is detected, the controller can increase pressure into the surgical tourniquet, thereby providing a means for ensuring that the flow of blood past the surgical tourniquet is occluded.

Alternately, the indication may comprise a blood oxygen saturation level or variation of the blood oxygen saturation level in the extremity of a patient to which a pressure cuff has been applied. A value associated with the blood oxygen saturation level or a variation in the blood oxygen saturation level may be detected using photo-optic techniques for measuring blood oxygen saturation, with a value associated therewith provided to the surgical tourniquet controller. Alternately, the signal transmitted to the controller may comprise a flag indicating a detection of increasing blood oxygenation downstream of the tourniquet. Additionally, the components used to detect blood oxygen saturation levels or variations thereof may be integrated within the surgical tourniquet and associated controller.

In a first embodiment, the present invention may be a surgical tourniquet controller which includes an occlusion sensor, and a means for increasing pressure in a surgical tourniquet when the occlusion sensor detects blood flow past the surgical tourniquet. The occlusion sensor may detect oscillometric indications or Korotkoff sounds as a means for detecting flow past the surgical tourniquet. The occlusion sensor alternately may detect blood oxygen saturation levels or variations thereof, such that a positive variation or a detected value above a threshold may be used as an indication of blood flow past the tourniquet.

In an alternate embodiment, the present invention comprises a method for controlling a surgical tourniquet. The method may include the steps of inflating a pressure cuff to an initial pressure, detecting blood flow past a pressure cuff when blood flows past the pressure cuff, incrementally increasing pressure in the pressure cuff in response to detected flow past the pressure cuff, determining whether the increased pressure in the surgical tourniquet has occluded blood flow past the tourniquet, and when blood flow has not been occluded, continuing to incrementally increase blood cuff pressure until blood flow past the tourniquet is occluded, or may additionally incrementally increase the cuff pressure until a threshold pressure is achieved.

In a still further embodiment, the present invention comprises a computer readable medium for providing instructions to a surgical tourniquet controller, the medium tangibly embodying instructions which, when executed by a computer, cause a surgical tourniquet controller to inflate a pressure cuff to an initial pressure, detect blood flow past a pressure cuff when blood flows past the pressure cuff, incrementally increase pressure in the pressure cuff when flow is detected past the pressure cuff, determine whether the increased pressure in the pressure cuff has occluded blood flow past the pressure cuff, and when blood flow has not been occluded, continue to incrementally increase blood pressure until blood flow past the pressure cuff is occluded.

Other features and advantages of the invention will be apparent from the following description of the preferred embodiment, and from the claims.

DETAILED DESCRIPTION OF THE INVENTION

Figure 1:
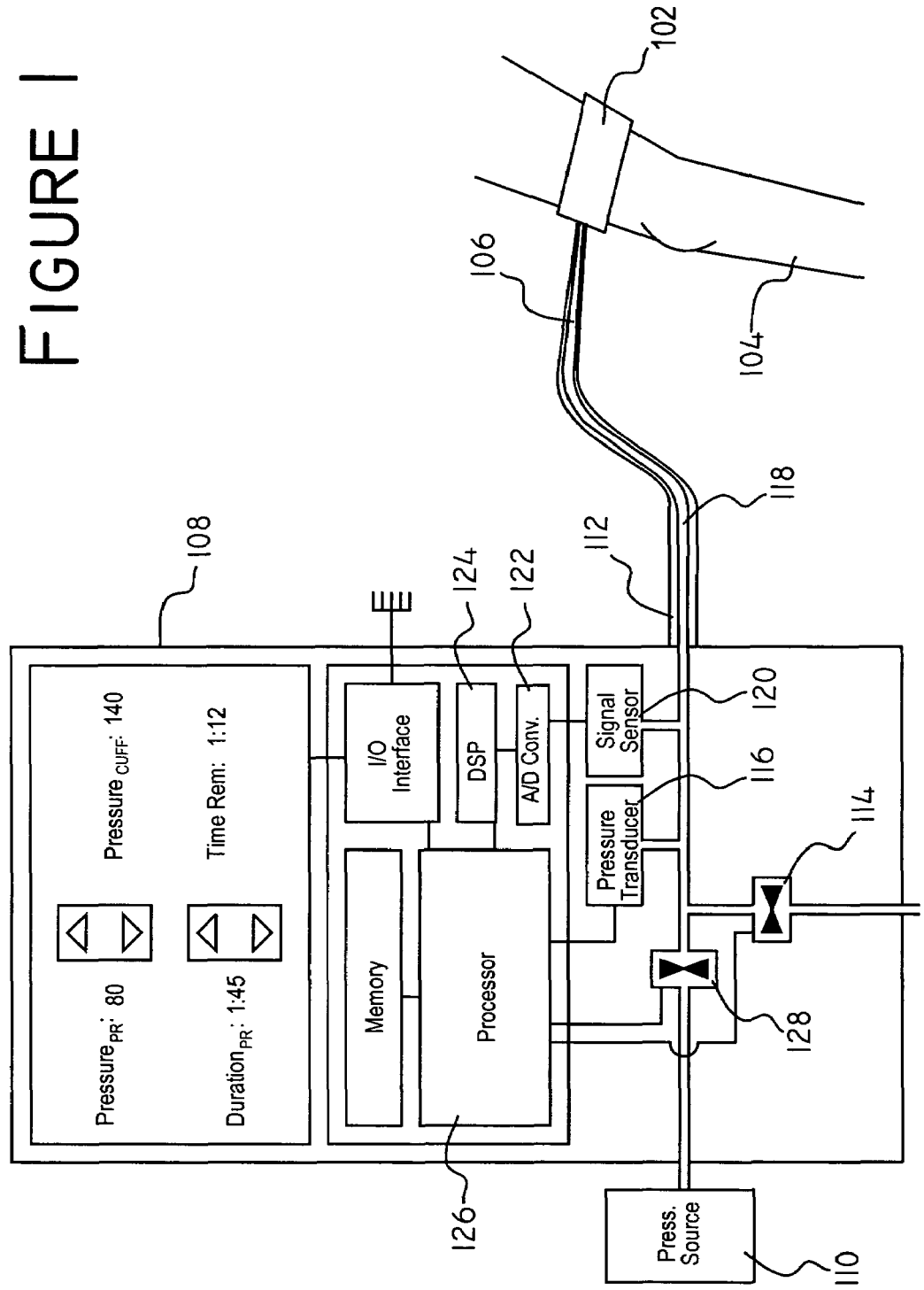
FIG. 1 is a block diagram illustrating the components of a basic surgical tourniquet controller according to the present invention.

Referring now to FIG. 1, wherein like reference numerals indicate like elements, there is shown the components of an embodiment of the present invention. A surgical tourniquet is a pressure cuff 102 containing a pressure chamber (not shown) which extends around the circumference of an appendage 104 in which it is desired to occlude blood flow. By increasing the pressure in the pressure chamber, the pressure cuff 102 compresses the appendage 104 until the constriction pressure exceeds the blood pressure, at which point internal veins and arteries close due to the inability of the blood pressure to overcome the pressure applied by the pressure cuff 102.

The pressure in the pressure chamber is controlled by adding or releasing a pressure medium 106 to or from the pressure chamber. The pressure medium 106 is a fluid allowing flow from the controller 108 into the pressure chamber. Pressure changes made to the pressure medium 106 at a location remote from the pressure cuff 102 are rapidly communicated to the pressure chamber when the pressure medium is a gas. Gaseous pressure mediums 106 are presently preferred, due to the ready availability of gases in the operating room environment. Although it is preferable to use air for the pressure medium 106 due to its free availability, other gasses or fluids may be used as conditions dictate. Furthermore, the use of a liquid, such as sterile distilled water, provides a better medium for the transmission of pressure signals from incipient blood flow.

Figure 3:
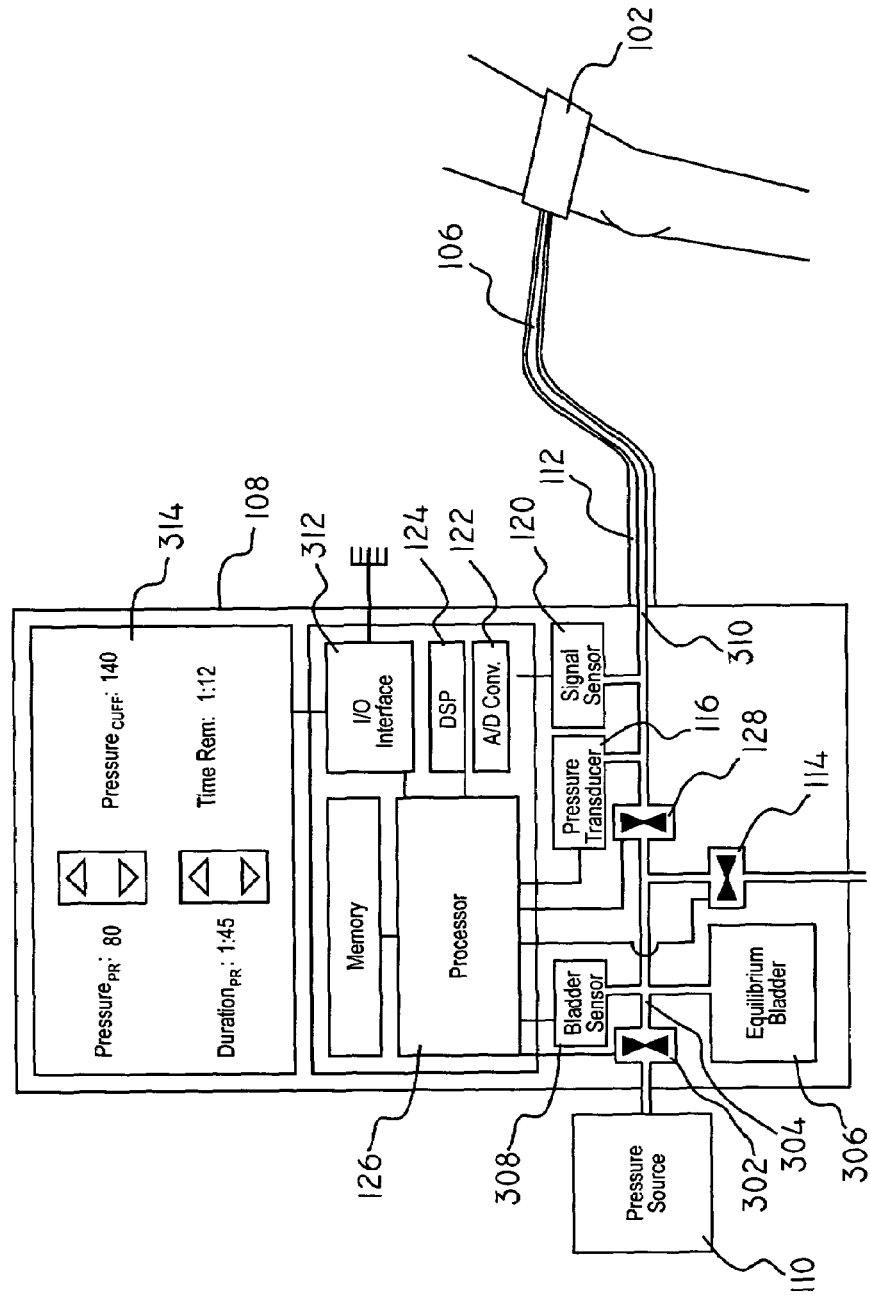
FIG. 3 is a block diagram illustrating the components of a surgical tourniquet controller according to the present invention, wherein the surgical controller includes additional controls and feedback loops for optimizing controller functionality.

In a typical controller 108, a source 110 of a pressurized flow medium is connected to the supply tube 112 to increase pressure in the pressure chamber, while a release valve 114 is provided to bleed pressure from the pressure chamber to decrease pressure. These components may be located in the controller 108 to minimize the components that have to be collocated with the patient (not shown) during a medical procedure. As described in applicant's prior disclosures, an improved controller 108 may be provided by incorporating an inflatable bladder into the controller 108 (as shown in FIG. 3), thus allowing rapid changes to the pressure condition of the pressure cuff 102.

The pressure in a typical pressure cuff 102 is pre-set based upon medical considerations, which include the blood pressure of the patient, as well as safety factors to ensure that blood flow is occluded when the pressure cuff 102 is pressurized. The tourniquet pressure may be set at 75-100 mm Hg above systolic blood pressure for a leg, or 50 to 75 mm Hg above systolic blood pressure for an arm. A pressure sensor 116 may be provided to measure the pressure in the pressure chamber of the pressure cuff 102. As the supply tube 112 provides flow communication between the pressure chamber and the controller 108, this pressure sensor 116 may be located in the controller 108 to further reduce the equipment which must be collocated with the patient.

The communicable path 118 that the pressure medium 106 forms may provide a path for flow signals to be transmitted from the pressure chamber to the controller 108. By placing a signal sensor 120 in communication with the pressure medium 106 either in the cuff or located in the controller, Korotkoff sounds and pressure variations indicating the onset of the flow of blood past a surgical cuff can be detected. From these indications, the controller can increase the cuff pressure if medically acceptable, and notify an operator of the incipient loss of blood occlusion. Rather than relying on blood pressure cuffs located on other portions of a patient's anatomy, the flow monitoring function is integrated within the tourniquet cuff, reducing the potential for disparities in measured conditions between a remote monitoring site and the tourniquet site. Furthermore, the direct monitoring of blood flow through the tourniquet allows the controller to use direct feedback, rather than a pressure off-set as a means of setting a pressure believed to be sufficient to occlude flow.

The selection of a fluid pressure medium is dependent on the capabilities of the sensor to be used to detect Korotkoff sounds or oscillometric variations in the cuff pressure. An incompressible liquid medium such as sterile distilled water provides an excellent medium for communicating pressure waves from a cuff through a supply tube to a remote controller. Concerns regarding the accidental discharge of the fluid medium into the surgical area should a cuff be accidentally punctured may necessitate the use of a gaseous medium such as air to alleviate the potential problems associated with an accidental puncture. The use of air as a pressure medium, with its compressible nature however, requires greater sensitivity on the part of the sensor, as well as more rigorous digital signal processing to ensure detection of flow signals.

The sensor can be placed either in the cuff or in a controller. Where the sensor is placed in the cuff, pressure signal damping associated with the compressible nature of a gaseous pressure medium may require additional sensitivity on the part of the signal sensor as signals may be damped between the patient's extremity and the controller 108. In such a situation, the use of an incompressible fluid as a pressure medium may alleviate a portion of the damping associated with the use of a compressible medium such as a gas.

The signal sensor 120 may be a piezoelectric sensor which generates an electrical signal proportionate to the signal being transmitted via the pressure medium 106 from the pressure chamber to the signal sensor 120. The sensitivity of the signal sensor 120 must be selected based upon the frequency and magnitude of the flow signal being used for signal detection. Such signal sensors 120 are known and used for ambulatory blood pressure monitoring systems. The output of the signal sensor 120 typically is an analog electrical signal corresponding to the pressure variations detected by the signal sensor 120.

A signal sensor 120 which measures Korotkoff sounds must measure the pressure variations with sufficient sensitivity to measure the frequencies characterizing the Korotkoff sounds. The sounds may have a frequency in the kilohertz range. Accordingly, the sensor must have sufficient sampling frequency sensitivity to provide pressure measurements several times during each cycle associated with the sound being sensed. The pressure variations associated with the Korotkoff sounds are of small magnitude, thus requiring the signal sensor 120 to be able to detect small variations around a base pressure. By using a signal sensor 120 selected to detect acoustic signals, pressure variations within the pressure chamber can be ignored or filtered out.

A signal sensor 120 which measures pressure variations associated with a patient's pulse may not requires as high a frequency detection capability as a sensor used to detect Korotkoff goods. Blood pulses during a surgical procedure are on the order of 100 pulses or less per minute, although the pulses may occur more frequently in smaller patients. Again, the signal sensor 120 must measure the pressure multiple times during each pressure pulse to be able to adequately measure the pulsing for surgical tourniquet control purposes. The pressure range associated with the pressure pulses is determined by the difference between cuff pressure and peak blood pressure, such that a signal sensor 120 having lower technical capabilities, and therefore lower cost, may be implemented.

The signal sensor 120 is preferably connected to an analog to digital converter 122 (A/D converter) that converts the analog output of the sensor to a digital signal having timing and magnitude components. The sampling rate of the A/D converter 122 must be sufficient to obtain several samples per sensor signal cycle. The digitized sensor signal may then be communicated to a digital signal processor 124 (DSP), which determines from the digitized data whether blood is flowing past the pressure cuff 102 of the surgical tourniquet.

The DSP 124 may preferably generate a positive flow signal when flow is detected. The positive flow signal may preferably be an indication of each time blood flow is detected. Since the blood pressure in a patient is cyclic, Korotkoff sounds or a pressure signal indicative of a pulse will occur each time the patient's heart pumps blood past the pressure cuff 102. Each detection results in the generation of a positive flow signal. Positive flow signals are communicated to the processor 126. When the processor 126 receives a positive flow signal indicating blood flow past the pressure cuff 102, the processor 126 causes the pressure in the pressure cuff 102 to be incrementally increased. Thus, each time a positive flow signal is received by the processor 126, the pressure in the pressure cuff 102 may be increased by opening the pressure source valve 128 to incrementally increase the pressure in the pressure cuff 102 until positive flow signals are no longer detected. The processor may then cause this pressure to be maintained, ensuring positive flow occlusion without relying on pressures significantly in excess of systolic blood pressure.

Basic Method of Controlling Pressure

Figure 2:
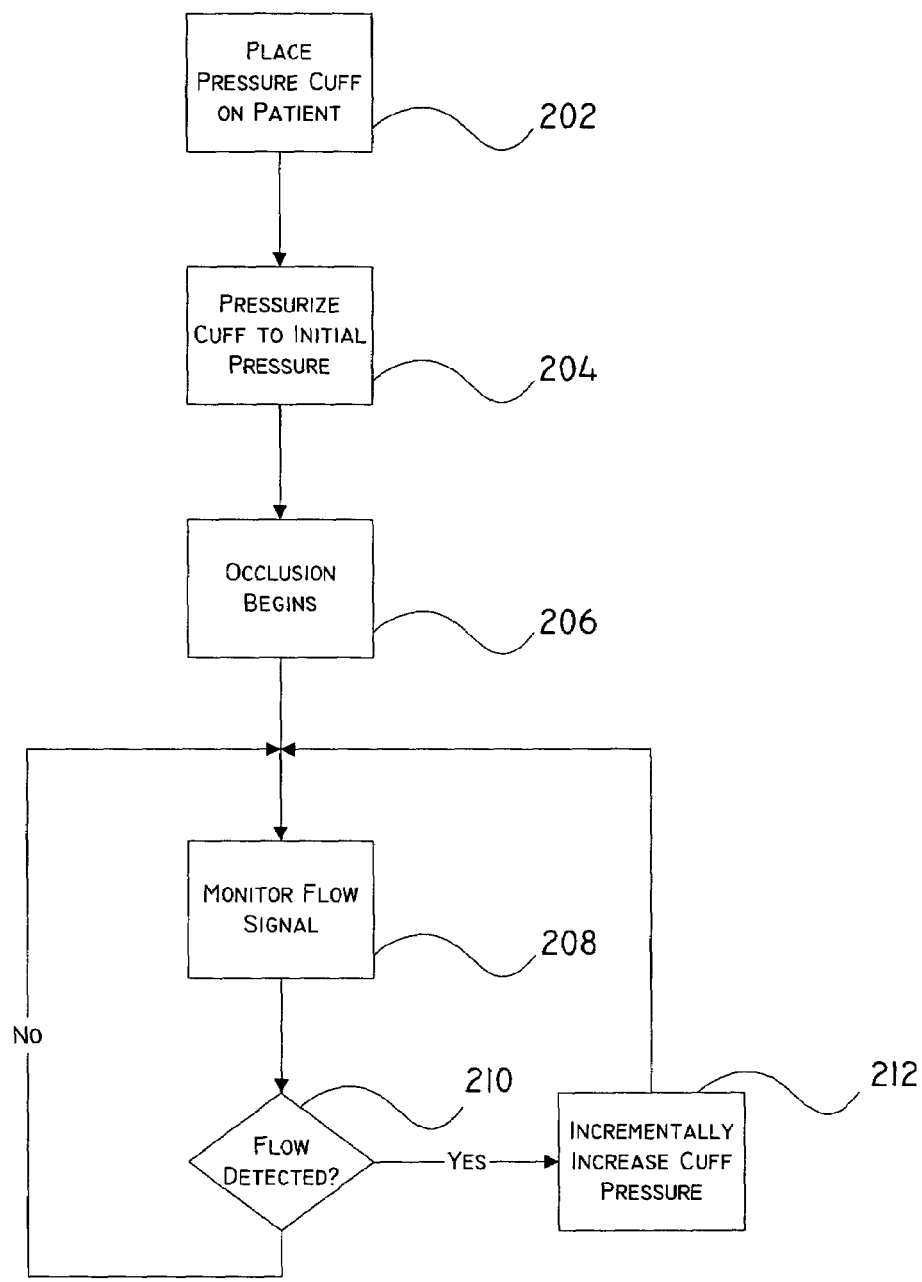
FIG. 2 is a process flowchart illustrating a method for controlling the occlusion of blood flow past a tourniquet according to the present invention.

The basic method of controlling a surgical tourniquet according to the present invention as shown in FIG. 2 thus relies on the generation of positive flow detection signals. The surgical tourniquet pressure cuff may be first placed 202 on the extremity of a patient whose blood flow is desired to be occluded. The pressure cuff may be initially pressurized 204 to an initial pressure, or may be left in an unpressurized state. An occlusion start signal may be used to initiate the pressurization 206 of the pressure cuff until blood flow is occluded. Once the occlusion process is initiated, the sensor monitors 208 blood flow in the extremity past the cuff, generating a positive flow signal each time flow is detected 210. The pressure in the cuff is incrementally increased 212 until no more positive flow signals are received by the pressure controller. This method has the further advantage of correcting for pressure changes that may occur due to manipulations of the extremity on which the pressure has been applied.

Preferred Method of Controlling Pressure

Although the above basic method of controlling pressure embodies the present invention, the presently preferred embodiment of the invention incorporates additional functions associated with the control of a surgical tourniquet pressure cuff 102. As disclosed in our earlier applications, the controller 108 may use programming which assists a person such as a physician or anesthesiologist (hereafter collectively referred to as the operator) in setting and utilizing a pressure cuff 102 connected to the controller 108. Basic functions performed by the controller 108 may be to inform the person utilizing the controller of time constraints associated with the use of the surgical tourniquet, or with the pressures utilized with the surgical tourniquet.

In the presently preferred embodiment of the present invention, as shown in FIG. 3, a pressure source 110 is provided. The pressure source 110 maybe a pump which compresses ambient air to form the pressure medium 106. Alternate embodiments may utilize an external pressure medium source, such as a compressed gas source, such as a pressure tank (not shown). Alternately, should the pressure medium in use be a fluid, an external pressure source could be employed. A one-way valve 302 is preferably provided to prevent pressure in the system from bleeding of through the pressure source 110. The one way valve 302 is able to be opened upon command from the processor 126. When the one way valve 302 is opened, flow is restricted such that flow only occurs from the pressure source 110 to the pressure cuff path 304.

An equilibrium bladder 306 may be provided to increase the rate at which pressure can be increased in a pressure cuff 102. By having an equilibrium bladder 306, rapid inflation of the pressure cuff 102 can be accomplished without requiring a high flow pressure source. An equilibrium bladder pressure sensor 308 may be provided to allow the processor 126 to monitor the pressure in the equilibrium bladder 306.

The pressure cuff 102 of the surgical tourniquet is connected to the controller 108 via a supply tube 112 which conducts the pressure medium 106. The tube is connected to a port 310 on the side of the controller 108, connecting the pressure cuff 102 to the pressure source 110. A source valve 128 is located adjacent to the port 310, and allows the pressure cuff 102 and supply tube 112 to be isolated from the pressure source, equilibrium bladder, and exhaust valves.

The flow signal sensor 120 and a cuff pressure transducer 116 are connected to the pressure cuff path 304 between the port 310 and the source valve 128, such that the flow signal sensor 120 and cuff pressure transducer 116 are not isolated from the pressure cuff 102. The cuff pressure transducer 116 may be used to determine variations in the cuff pressure, such as due to a leak, or from changes resultant from the repositioning of a patient during a procedure.

The output of the signal sensor 120 is provided to an A/D converter 122, which passes the digitized signal to the digital signal processor 124, where the digitized output is analyzed for the presence of a flow signal. If a flow signal is detected, the central processor is so informed.

The controller 108 is also preferably provided with an input/output interface 312, which coordinates the flow of information to and from the controller 108. A first function of the I/O interface may be to allow an operator to provide input to the controller 108 through an operator interface 314, which may be a touch screen display on which menu-structured queries can be presented.

Figure 4A:
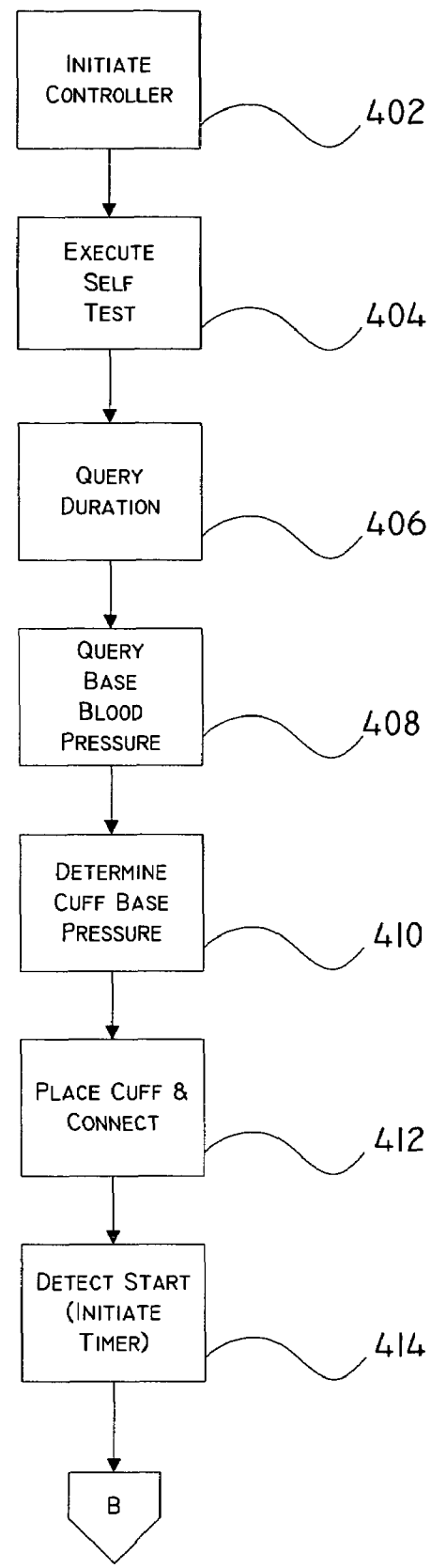
FIG. 4 is a process flowchart illustrating a method for controlling the occlusion of blood flow past a tourniquet utilizing blood pressure feedback such as in the system shown in FIG. 3.
Figure 4B:
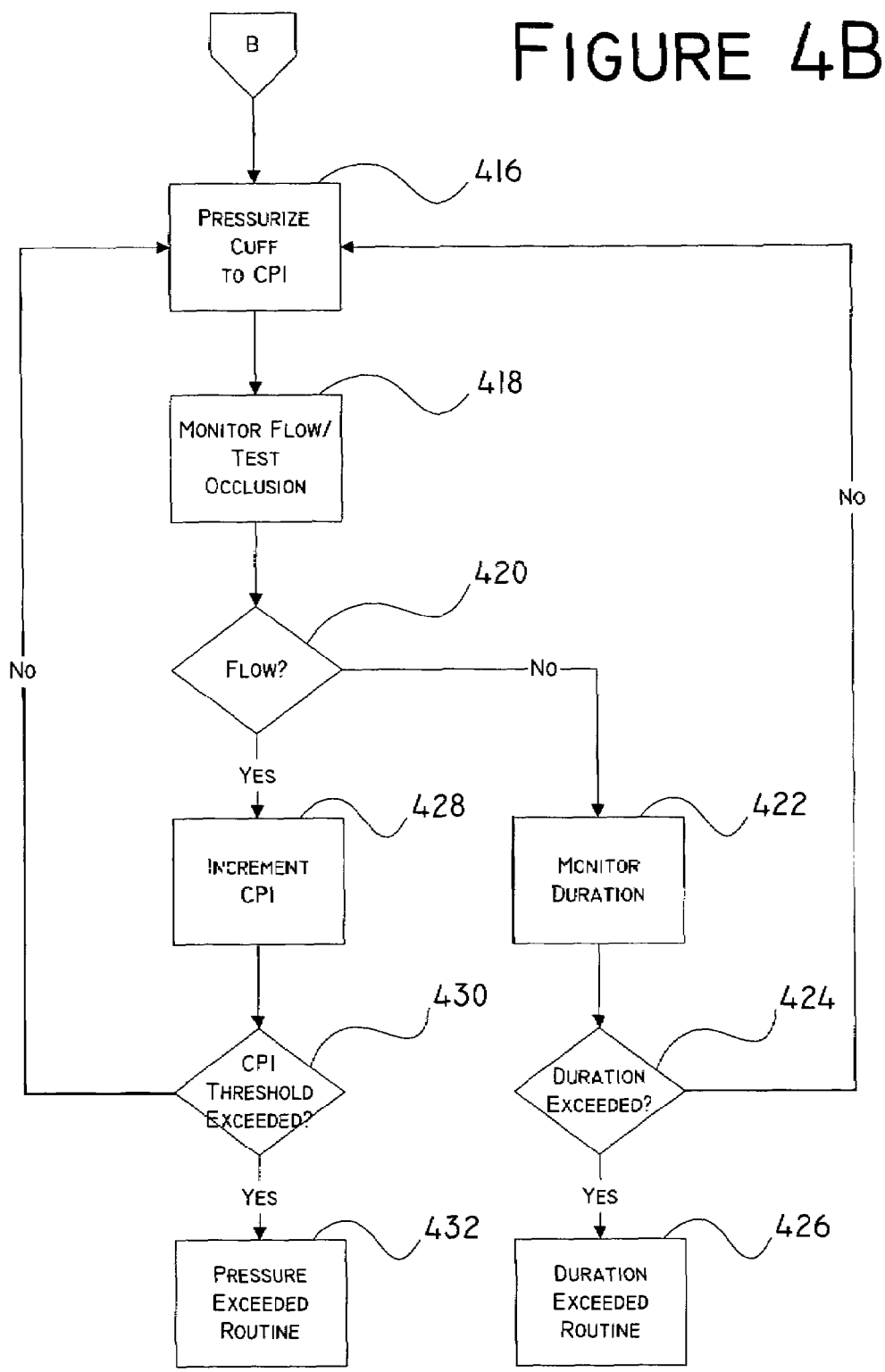

Accordingly, as shown in FIG. 4, the first step in the method of utilizing the presently preferred controller comprises first initiating 402 the controller. The initialization routine may preferably include the execution 404 of an internal self test verifying the circuitry of the controller, and the execution of the basic controller programming. Once the controller has performed these initiation functions, the controller may query 406 an operator to determine a desired inflation duration. This query can be conducted by displaying a duration setting field for an operator. Once the duration has been determined, the controller may also query 408 the operator for a base blood pressure. Where ausculitc signal detection is utilized, the pressure cuff must be initially pressurized to a level sufficient to at least partially occlude blood flow past a pressure cuff. Where oscillometric detection is implemented, sufficient initial pressure must be present in the pressure cuff to provide an adequate signal path between the pressure cuff and the sensor. Initial pressures may be suggested to the operator based on the extremity on which the tourniquet is to be placed, and/or the operator may be queried as to the blood pressure of the patient from which an initial pressure can be derived.

Once an initial pressure has been identified by an operator or set based on pre-programmed instructions, the controller may determine 410 a cuff base pressure based on the input provided by the operator. Where the operator has provided patient blood pressure, the controller may set an initial base pressure as an increment above patient blood pressure. Where the operator has specified a desired cuff pressure, the initial base pressure may be set equal to the desired cuff pressure. The cuff pressure inflation (CPI) may then be set to the base pressure.

Next, the pressure cuff may be placed 412 around the extremity of a patient for which blood flow is desired to be occluded. The pressure chamber of the cuff may then be connected by a pressure tube to the controller.

Once an occlusion initiation signal is detected 414 by the controller, the controller pressurizes 416 the pressure cuff to the CPI, and the sensor monitors 418 blood flow past the pressure cuff. As long as no blood flow past the pressure cuff is detected, the pressure controller monitors 418 the pressure in the cuff, and maintains the pressure in the cuff, while monitoring 422 the amount of time for which the pressure has been applied. Once it is determined 424 that the pressure has been applied for the selected duration, the controller may execute 426 a duration exceeded routine, including informing the operator that the programmed duration has expired. Alternately, the operator may manually end the blood flow occlusion by signaling the pressure controller to depressurize the cuff. If the pre-set duration has expired, the controller may signal the operator before depressurizing the cuff, allowing the operator to set an additional incremental duration.

The controller may also monitor the cuff pressure to ensure that safe pressures are maintained during the period in which blood flow is occluded. A maximum pressure may be pre-set by an operator, or a maximum pressure may be preset in memory associated with the controller. If a cuff pressure threshold is exceeded, a pressure exceeded routine may be implemented.

Once the pressure cuff has been pressurized to the initial pressure, blood flow past the pressure cuff may be monitored 418. If it is determined 420 that blood is flowing past the pressure cuff, the pressure controller determines whether an incrementally increased 428 pressure would exceed the maximum pressure. If it is determined 430 that the incrementally increased pressure would not exceed the maximum pressure, the pressure controller directs pressurization 416 of the pressure cuff to the incrementally increased pressure. If it is determined 430 that the incrementally increased pressure would exceed the maximum pressure, a pressure exceed routine may be executed 432, including generating an alarm to inform an operator that blood flow is not being fully occluded, and that the maximum pressure threshold has been achieved. At this point, the operator may over-ride the maximum pressure and set a higher maximum pressure, or may cause a medical procedure to be ended due to the blood flow past the tourniquet. If the maximum pressure is re-set to a higher level, the pressure controller may continue to incrementally increase the cuff pressure in response to positive flow signals until blood flow is occluded, or until the new maximum pressure is achieved.

Alternate Embodiments

Figure 5:
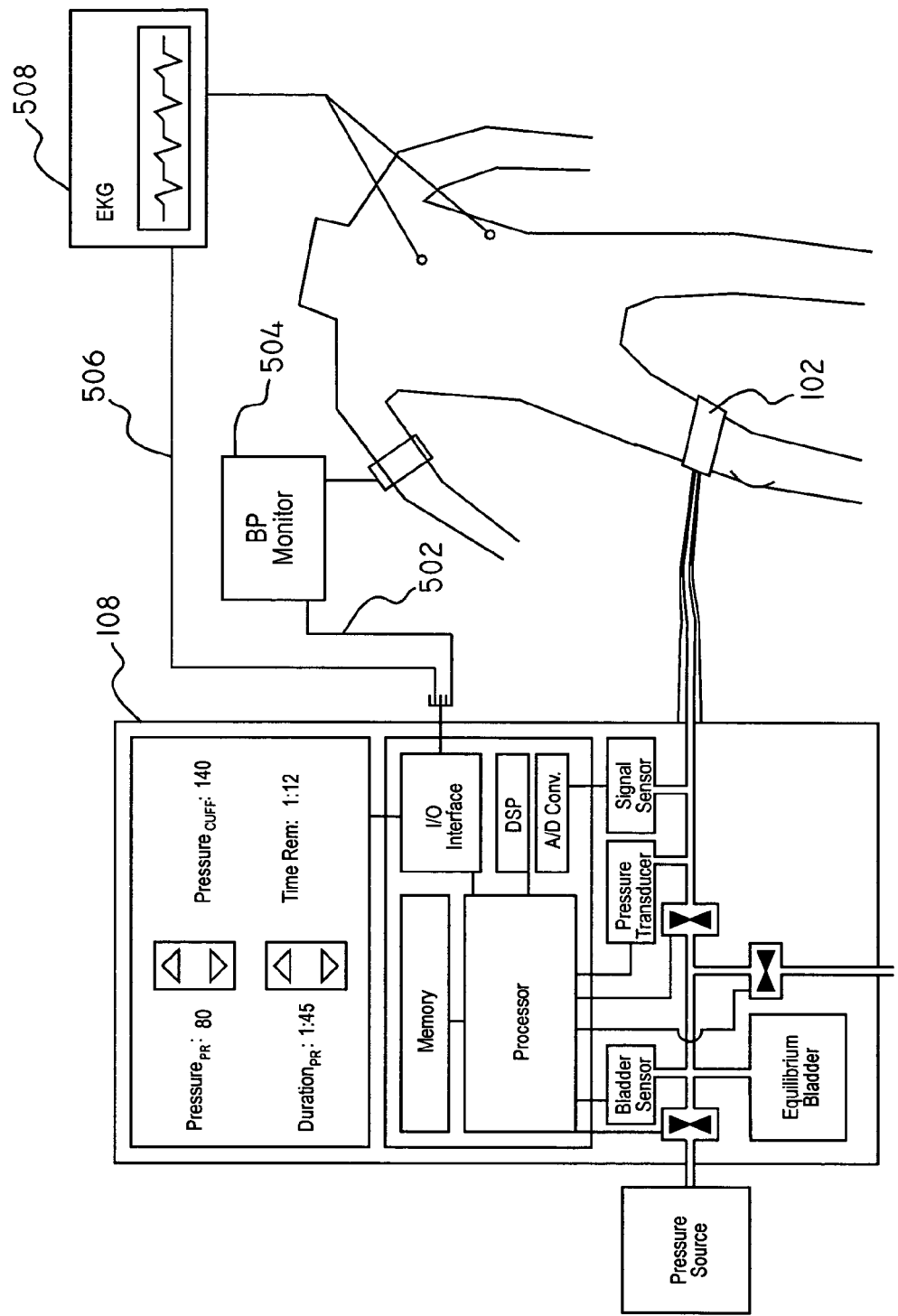
FIG. 5 is a block diagram illustrating the use of the present invention in an operating room environment in accordance with the present invention.

In addition to the feedback provided by the flow detection sensor, the surgical tourniquet controller may be provided with additional feedback sources. As shown in FIG. 5, a feedback signal 502 informing the controller of systolic pressure from a blood pressure monitor 504 may be implemented such that the controller may set cuff pressure dependant upon the systolic pressure, while providing flow detection measurement to ensure that blood flow is occluded. The systolic pressure feedback system may utilize pressures determined by invasive or non-invasive methods.

An alternate feedback loop may be provided by providing a heart rate or electrocardiogram signal (EKG) 506 from an EKG monitor 508 to the controller 108, allowing flow signals to be correlated to heart beats. Providing a heart rate or EKG signal 506 would allow non-flow related noises to be filtered out based on the beating of the heart.

Alternately, detected signals and associated data could be transmitted from the STC to other medical equipment by implementation of an output port (not shown). Such a port could be utilized to allow data associated with a medical procedure to be recorded and stored for addition to a patient medical record, or to a controller utilization record.

Figure 6:
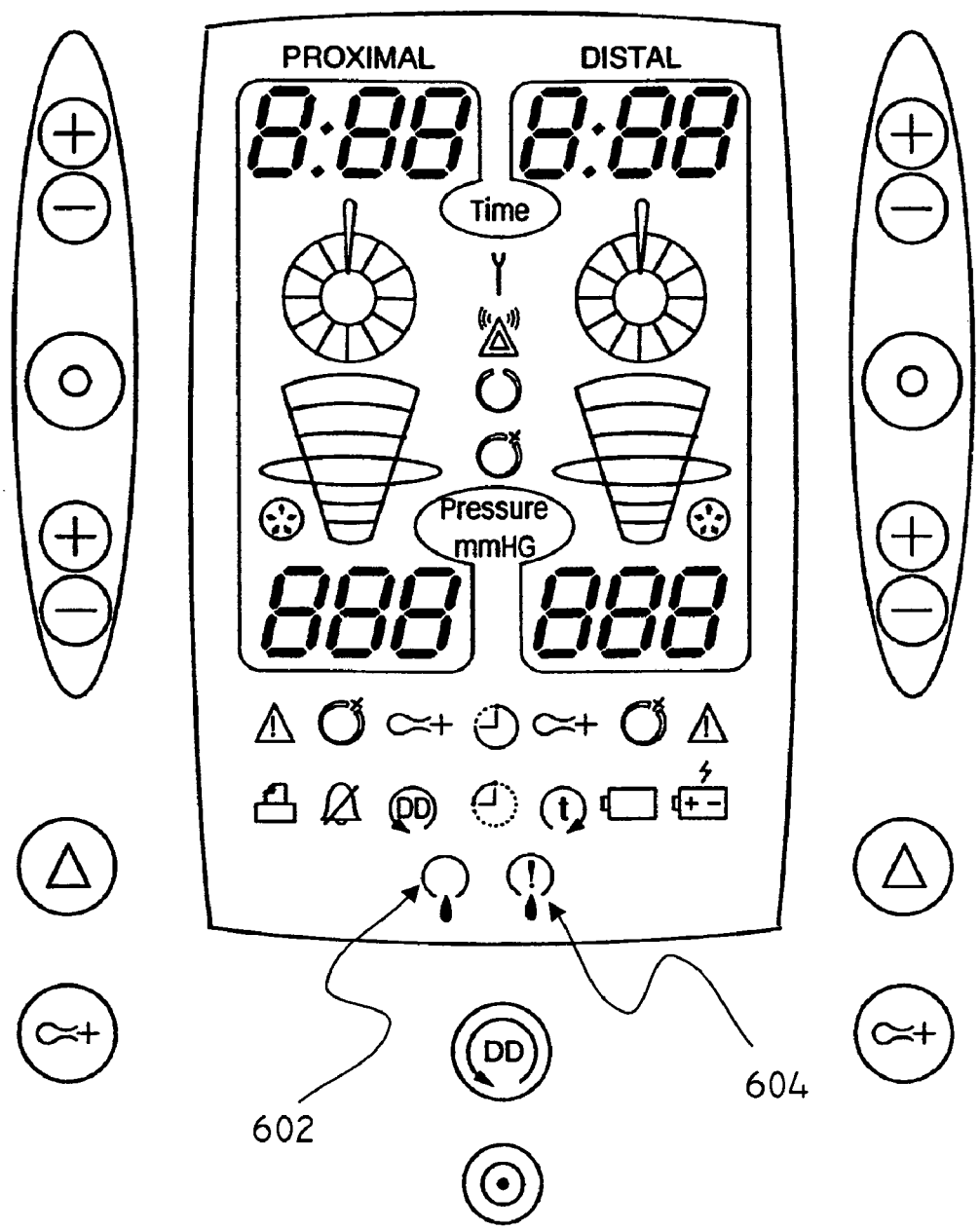
FIG. 6 is an illustration of an operator input/output interface for use with the present invention.

As shown in FIG. 6, the display of the STC may include multiple functions. The display may include an iconic indicator 602 of detected blood flow past the pressure cuff, or a iconic indication 604 indicating that a maximum pressure has been reached and blood flow past the pressure cuff is still being detected.

The flow detection indicators may be programmed to illuminate for a timed period after a flow detection occurs, such that after a specific period of time or number of heartbeats, the indicator is extinguished unless additional flow past the pressure cuff is detected.

Figure 7:
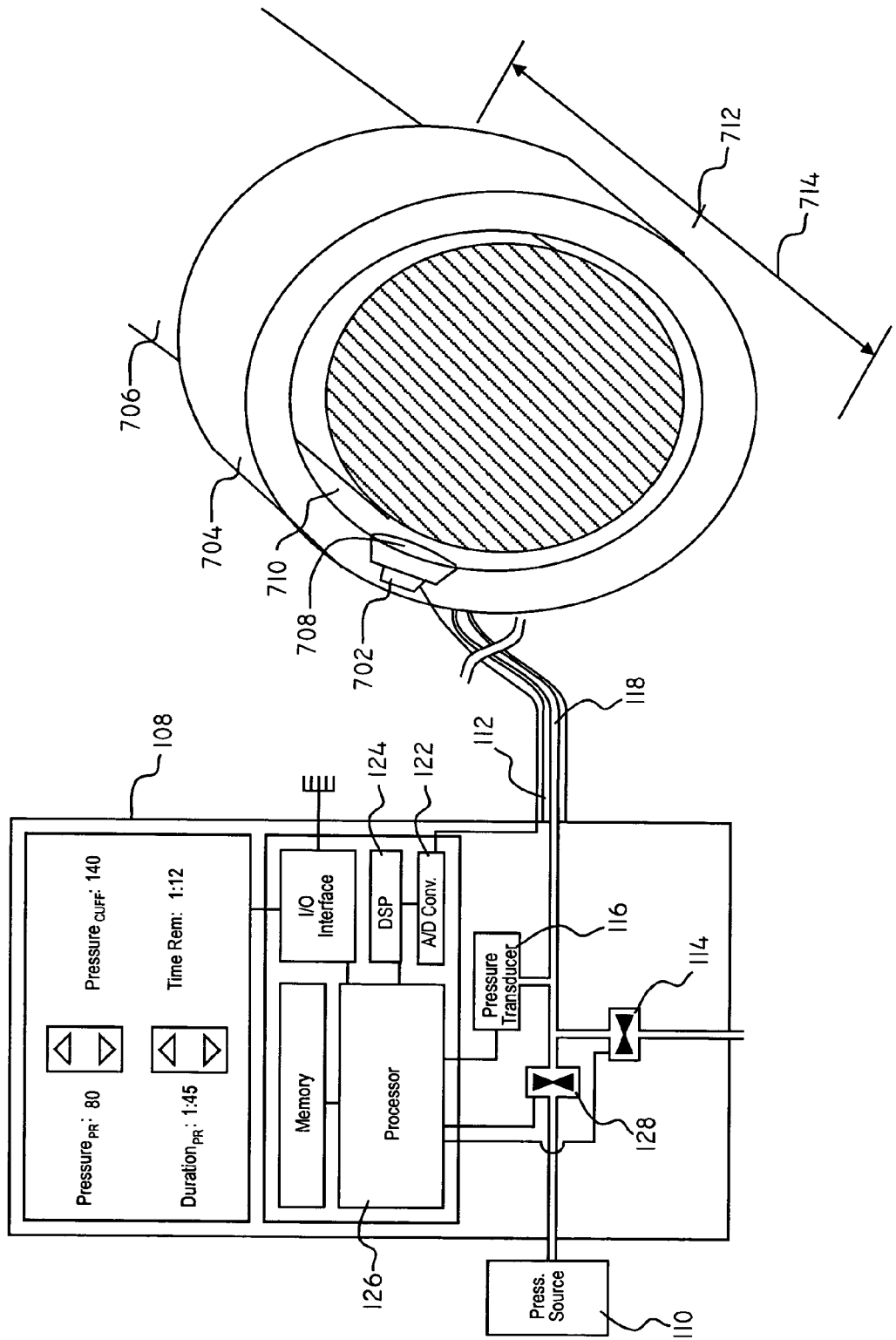
FIG. 7 is a block diagram illustrating the components of a basic surgical tourniquet controller according to the present invention utilizing a cuff mounted photometric blood oxygen saturation monitor.

As shown in FIG. 7, a photometric sensor 702 may be implemented as the flow detection monitor by integrating the photometric sensor 702 with the pressure cuff 704 surrounding the extremity 706 of interest. Sensors, such as those marketed by Oxford Optronix as models M8P300C, M8300CP, or M8P300T may be formed into the pressure cuff 704 such that a portion 708 of the inner surface 710 of the pressure cuff 704 is formed by the sensor 702, thus ensuring contact between the sensor and the skin of the patient. Care must be taken to ensure that the sensor is flush with the inner surface 710, to prevent the force being applied by the pressure cuff 702 from being concentrated in one location, thus reducing the effect of the pressure cuff 702.

Signal bands from the photometric sensor may be routed through the interior of the pressure cuff to a location adjacent to the pressure feed for the pressure cuff, and through the outer wall of the pressure cuff so that they may be routed with a pressure supply tube.

The A/D circuitry of the controller may be provided with circuitry to enable the photometric sensor, such as a reference signal or power supply, or the photometric sensor can be monitored from equipment separate from the tourniquet controller, but communicably connected to the surgical tourniquet controller to allow communication of flow detections to the surgical tourniquet controller processor.

Figure 8:
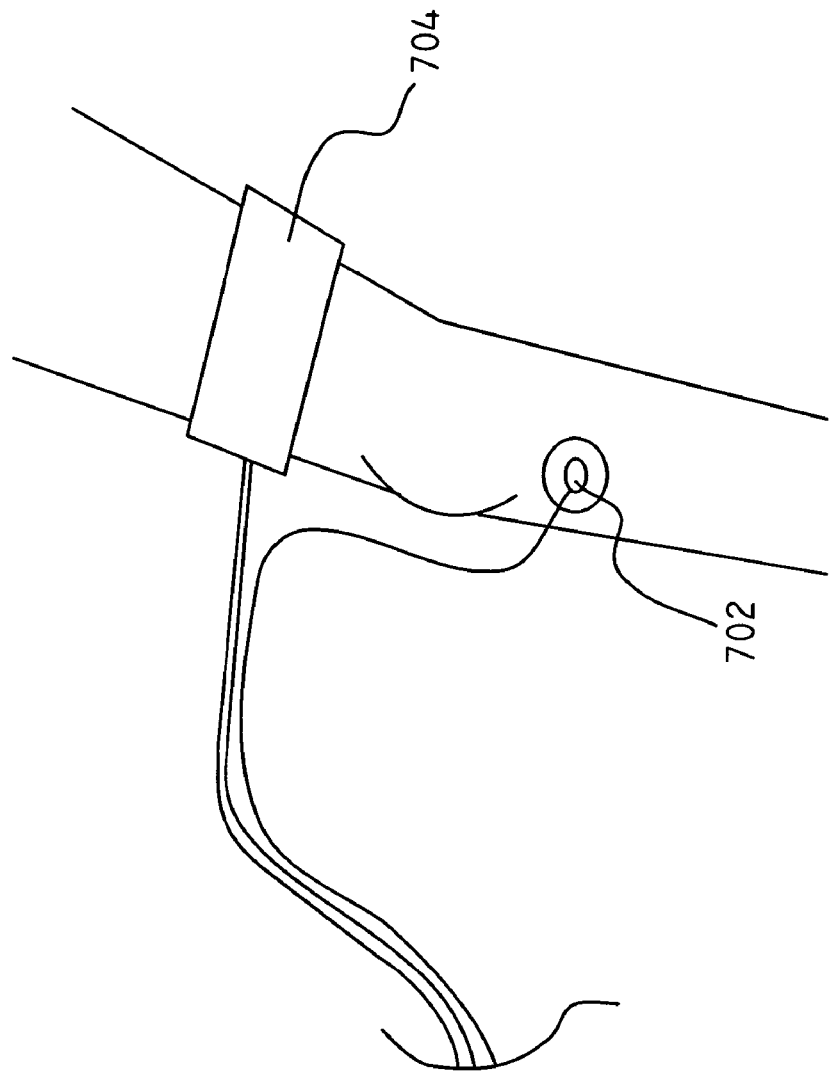
FIG. 8 is an illustration of a distally located blood oxygen saturation sensor being used with a surgical tourniquet.

As shown in FIG. 8, the photometric sensor 702 may be located distally from the pressure cuff 704, however such a location may be subject to a delay between when oxygenated blood begins to flow past the pressure cuff 704 and when the oxygenated blood is detected at the blood oxygen saturation sensor 702, especially at low flow levels past the pressure cuff 704. This effect highlights the importance of the positioning of the photometric sensor.

If a photometric sensor 702, such as that shown in FIG. 7, is placed on the upstream side of the pressure cuff 704, motion of blood above the cuff 704 may cause variations in the oxygen saturation level unrelated to the success of the cuff 704 in occluding blood flow. Accordingly, it is preferable to locate the photometric sensor 702 at the mid-point 714 of the cuff span 716, or downstream of the mid-point of the cuff span 716 to minimize oxygen saturation variations resultant from effects other than blood flow past the pressure cuff 704.

Figure 9:
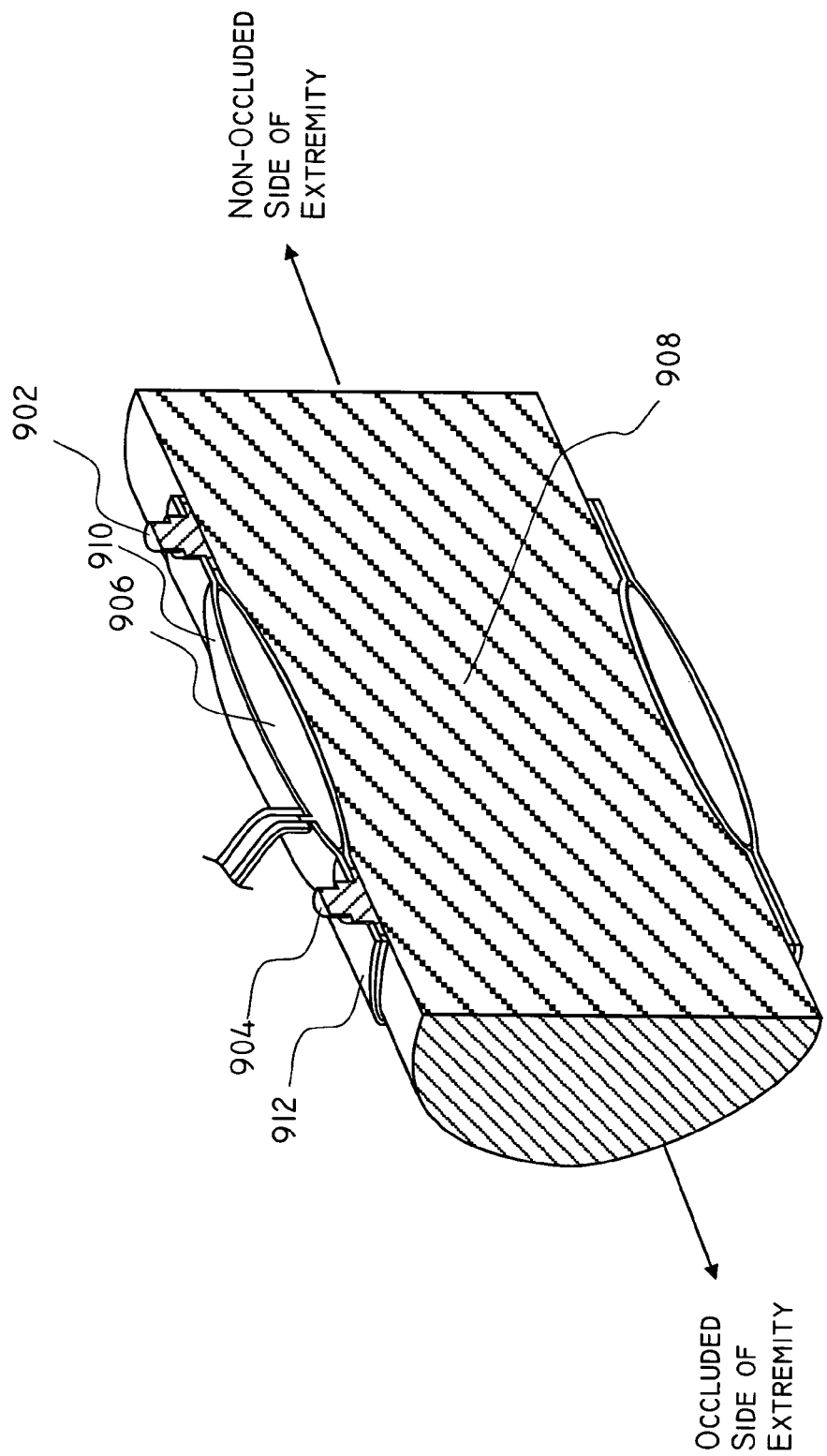
FIG. 9 illustrates a perspective view in cutaway of surgical tourniquet pressure cuff incorporating occluded and non-occluded blood oxygen saturation sensors as applied to the extremity of a patient.

FIG. 9 illustrates an alternate embodiment utilizing dual photometric blood oxygen saturation sensors 902, 904 to allow monitoring of blood oxygen saturation both above and below the pressure cuff. A first blood oxygen saturation sensor 902 may be located above the pressure bladder 906 and the occlusion zone 908. Although the illustration shows the sensor 902 located adjacent to the pressure bladder 906, the first blood oxygen sensor may be located further away from the pressure bladder 906 in order to ensure that sub-cutaneous blood being monitored is circulating, as opposed to blood immediately above the pressure bladder which may be subject to limited circulation due to the occlusion created by the inflated pressure bladder 806.

The second blood oxygen saturation sensor 904 may be located below the occlusion zone 908, such that sub-cutaneous blood being monitored is not subject to circulatory flow while the pressure bladder is effectively occluding blood flow, but which would detect increasing oxygenation of the subcutaneous blood flow should blood begin to flow past the inflated pressure bladder.

Figure 10:
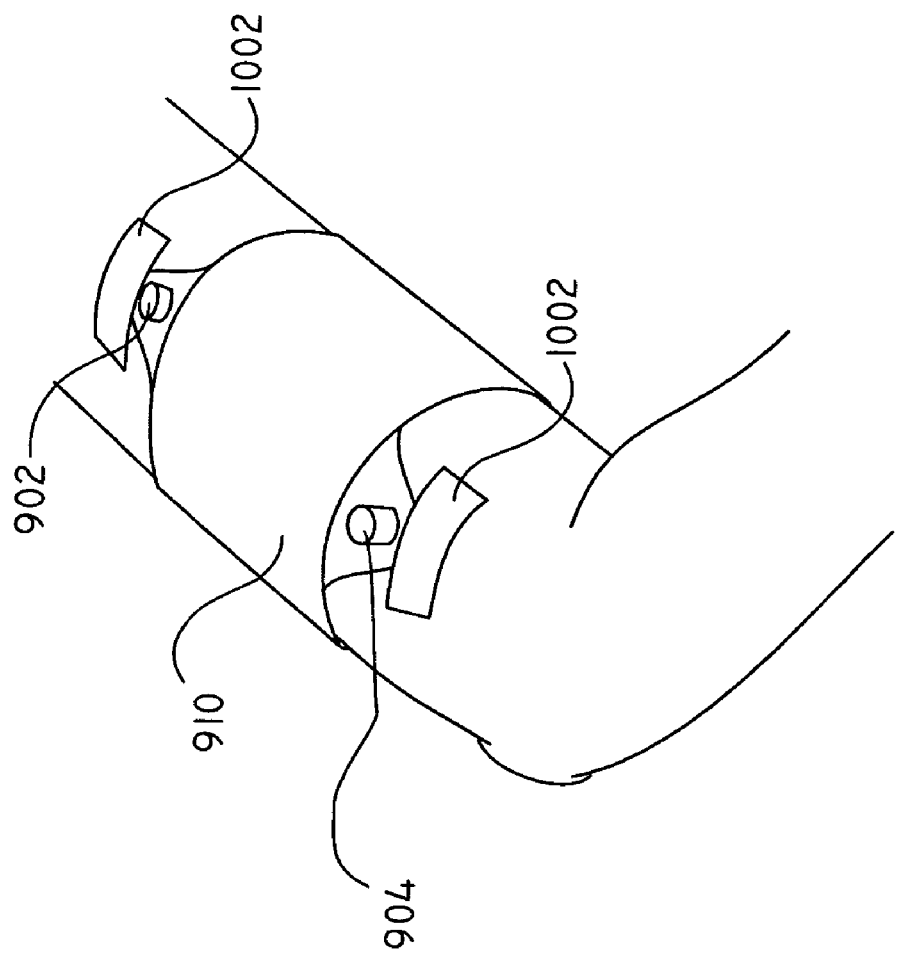
FIG. 10 illustrates a surgical tourniquet pressure cuff incorporating occluded and non-occluded blood oxygen saturation sensors connected to flaps integrated with the pressure cuff.

Also as shown, the sensors 902, 904 do not need to be mounted underneath the pressure bladder 906, but may be integrated with the pressure cuff assembly 910 outside of the region in which the pressure bladder 906 is located. It may be beneficial to ensure that the sensors 902, 904 remain in contact with the skin of the patient to whom the surgical tourniquet is applied, in order to ensure the proper operation of the sensors. Such contact may be ensured by extending the pressure cuff sheath 912 around the entire extremity in the area in which the sensor or sensors are mounted. Alternately, the portion of the sheath in which the sensor or sensors are mounted may be in the form of a tab, such as shown in FIG. 10, such that the tab may be taped or otherwise adhered to the skin of the patient.

Flow detections may be based either on a positive increase in the blood oxygen saturation level, or based on a blood oxygen saturation level exceeding a threshold value. The blood oxygen saturation level above the tourniquet may be used as a reference for determining a value at which flow may be considered no longer occluded below the surgical tourniquet. Accordingly, monitoring circuitry for the photometric sensor must be capable of detecting or recognizing changes at a level sufficient to provide a useful detection level.

The present invention may be embodied in other specific forms without departing from the spirit or essential attributes of the invention. Accordingly, reference should be made to the appended claims, rather than the foregoing specification, as indicating the scope of the invention.

What is claimed is:

1. A surgical tourniquet controller, said controller comprising:
    a pressure source, said pressure source supplying a pressure medium at a sufficient pressure to pressurize a pressure cuff being used as a surgical tourniquet;
    a pressure port, said pressure port allowing a pressure medium to be supplied to a pressure cuff;
    a source valve, said source valve interposed between said pressure source and said pressure port;
    an occlusion sensing means for detecting blood flow past a pressure cuff; and
    a processor, said processor communicably connected to said occlusion sensing means, said processor further communicably connected to said source valve;
    wherein said processor instructs said source valve to increase the pressure in a pressure cuff when said occlusion sensing means detects blood flow past the pressure cuff.

2. A surgical tourniquet controller according to claim 1, wherein said occlusion sensing means comprises a pressure transducer for detecting pressure variations in the pressure cuff indicative of blood flow past the pressure cuff.

3. A surgical tourniquet controller according to claim 2, wherein said occlusion sensing means further comprises a processor having instructions for detecting oscillometric pressure variations indicative of blood flow past the pressure cuff.

4. A surgical tourniquet controller according to claim 2, wherein said occlusion sensing means further comprises a processor having instructions for detecting Korotkoff sounds indicative of blood flow past the pressure cuff.

5. A surgical tourniquet controller according to claim 2, wherein said occlusion sensing means further comprises signal processing circuitry to detect oscillometric variations in the pressure indicative of blood flow past the pressure cuff.

6. A surgical tourniquet controller according to claim 2, wherein said occlusion sensing means further comprises signal processing circuitry to detect Korotkoff sounds indicative of blood flow past the pressure cuff.

7. A surgical tourniquet controller according to claim 1, further comprising a pressure threshold value, wherein said processor instructs said source valve to increase the pressure in a pressure cuff only when the increased pressure would not exceed the pressure threshold value.

8. A surgical tourniquet controller according to claim 1, further comprising a pressure relief valve, said pressure relief valve having a pre-determined pressure threshold value, said pressure relief valve being connected to said pressure port such that if a pressure in said pressure port exceeds said pressure threshold value, said pressure relief valve vents said pressure port.

9. A surgical tourniquet controller according to claim 1, wherein said occlusion sensing means comprises a photometric sensor for measuring blood oxygen saturation.

10. A surgical tourniquet controller according to claim 9, wherein said surgical tourniquet controller further comprises a pressure cuff, said photometric sensor being located on an inner surface of said pressure cuff.

11. A surgical tourniquet controller according to claim 10, wherein said photometric sensor comprises a laser doppler perfusion monitor.

12. A surgical tourniquet controller according to claim 9, wherein said surgical tourniquet controller further comprises a processor having instructions for detecting variations in sensed blood oxygen saturation levels indicative of blood flow past the pressure cuff.

13. A surgical tourniquet controller according to claim 9, wherein said surgical tourniquet controller further comprises signal processing circuitry for detecting variations in sensed blood oxygen saturation levels indicative of blood flow past the pressure cuff.

14. A method for controlling a surgical tourniquet, said method comprising the steps of:
    inflating a pressure cuff to an initial pressure;
    incrementally decreasing pressure in the pressure cuff until flow is detected by a flow sensor past the pressure cuff;
    increasing the pressure in the pressure cuff a pre-set amount;
    monitoring the flow sensor to detect flow past the pressure cuff; and
    when flow is detected past said pressure cuff, incrementally increasing pressure in said pressure cuff until flow is no longer detected.

15. A method for controlling a surgical tourniquet according to claim 14, further comprising the step of:
    when flow is detected past said pressure cuff, increasing the pressure in said pressure cuff a pre-set amount once flow is no longer detected past said pressure cuff.

16. A method for controlling a surgical tourniquet according to claim 14, further comprising the step of:
    receiving a desired inflation duration;
    starting a timer when the pressure cuff is initially inflated; and
    deflating the pressure cuff when the desired inflation duration has occurred.

17. A method for controlling a surgical tourniquet according to claim 14, further comprising the steps of:
    receiving a desired inflation duration;
    starting a timer when the pressure cuff is initially inflated;

informing an operator when the desired inflation duration has occurred.

18. A method for controlling a surgical tourniquet according to claim 14, further comprising the steps of:
  determining a threshold pressure above which the pressure cuff should not be inflated;
  ceasing pressure increases when the threshold pressure is achieved; and
  informing an operator that the threshold pressure has been achieved.

19. A method for controlling a surgical tourniquet according to claim 14, further comprising the steps of:
  receiving a threshold pressure above which the pressure cuff should not be inflated from an operator;
  ceasing pressure increases if the threshold pressure is reached; and
  informing an operator that the threshold pressure has been reached.

* * * * *